United States Patent
Ortashi et al.

(10) Patent No.: US 9,701,552 B1
(45) Date of Patent: Jul. 11, 2017

(54) SYNTHESIS OF SILVER NANOPARTICLES USING FUNGI

(71) Applicant: KING SAUD UNIVERSITY, Riyadh (SA)

(72) Inventors: Khalid Mustafa Osman Ortashi, Riyadh (SA); Manal Ahmed Gasmelseed Awad, Riyadh (SA); Awatif Ahmed Hendi, Riyadh (SA); Abeer Ramadan Mohamed Abdelaziz, Riyadh (SA); Ahmed Sameer Ahmed Hendi, Riyadh (SA); Abdulhakeem Abdulmuhseen Alahmed, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/338,259

(22) Filed: Oct. 28, 2016

(51) Int. Cl.
*C02F 1/50* (2006.01)
*A01N 63/04* (2006.01)
*C12P 3/00* (2006.01)

(52) U.S. Cl.
CPC .............. *C02F 1/50* (2013.01); *A01N 63/04* (2013.01); *C12P 3/00* (2013.01); *C02F 2303/04* (2013.01); *C02F 2305/08* (2013.01)

(58) Field of Classification Search
CPC ........ A01N 59/16; A01N 25/34; A01N 63/04; C02F 1/50; C02F 1/505; C02F 2303/04; C02F 2305/08; C12P 3/00
See application file for complete search history.

(56) References Cited

U.S. PATENT DOCUMENTS

| 8,394,421 | B2 | 3/2013 | Mansoori | |
| 2007/0218555 | A1* | 9/2007 | Paknikar | A01N 59/16 435/410 |
| 2008/0181843 | A1* | 7/2008 | Lu | C02F 1/283 423/634 |

OTHER PUBLICATIONS

Sarkar et al., "Alternaria Alternata Mediated Synthesis of Protein Capped Silver Nanoparticles and their Genotoxic Activity," Digest Journal of Nanomaterials and Biostructures, vol. 6, No. 2, Apr.-Jun. 2011, p. 563-573.

* cited by examiner

*Primary Examiner* — Lucas Stelling
(74) *Attorney, Agent, or Firm* — Richard C. Litman

(57) ABSTRACT

A method of preparing metal nanoparticles from fungi includes preparing a biomass of fungal cells; providing an aqueous solution including a metal salt; mixing the biomass of fungal cells with the aqueous solution of metal salt; and incubating the resulting mixture at a temperature range of 35° C. to 60° C. to produce the metal nanoparticles.

8 Claims, 3 Drawing Sheets

SYNTHESIS OF SILVER NANOPARTICLES USING FUNGI

BACKGROUND OF THE INVENTION

1. Field of the Invention

The present invention relates generally to metal nanoparticle synthesis, and particularly, to a green method of preparing silver nanoparticles using fungal biomass culture.

2. Description of the Related Art

Nanoparticles exhibit completely new or improved properties compared to their corresponding bulk materials. Nanotechnology is a deliberate manipulation of matter at size scales of less than 100 nm and holds the promise of creating new materials and devices which take advantage of unique phenomenon realized at those nanoscales. Because of their size, catalytic property, ability to deliver drug, increased efficacy, and decreased toxicity, nanotechnology finds applications in various fields including healthcare, defense and day-to-day life.

There has been a search for greener production alternatives of metal nanoparticles. Both unicellular and multicellular organisms have been found to produce inorganic materials either intra- or extracellularly. For example, a large number of fungal strains are capable of synthesizing silver nanoparticles (AgNPs) extracellularly.

Clean water (i.e., water that is free of toxic chemicals and pathogens) is essential to human health. In countries such as India, 80% of the diseases are due to bacterial contamination of drinking water. Research is underway to use advance nanotechnology in purification of drinking water. Preliminary studies have shown that a 20 ppm silver colloidal suspension (~30 nm diameter) in purified water has a 100% cure rate for malaria. Spherical aggregates of nanoparticles that have a similar size and shape to the resin beads already used in water purification. The protection of water treatment systems against potential chemical and biological terrorist acts is also becoming a critical issue in water resources planning. Nanoparticles can also be designed and synthesized to act as either separation or reaction media for pollutants. Recent applications of silver nanoparticles have included open wound and burn treatment.

Thus, a method of synthesizing noble metal nanoparticles from fungi thereby solving the aforementioned problems is desired.

SUMMARY OF THE INVENTION

A method of preparing metal nanoparticles from fungi include preparing a biomass of fungal cells; providing an aqueous solution including a metal salt; mixing the biomass of fungal cells with the aqueous solution of metal salt; and incubating the resulting mixture at a temperature range of 35 to 60° C. to produce the metal nanoparticles, wherein the incubating step is preferably performed in the dark for at least 24 hours.

A method of decontaminating water, e.g., purifying drinking water and/or treating sewage water, comprises contacting the water with an effective amount of the silver nanoparticles produced from fungal cells according for a time sufficient to remove microorganisms or pollutants from said sewage water.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
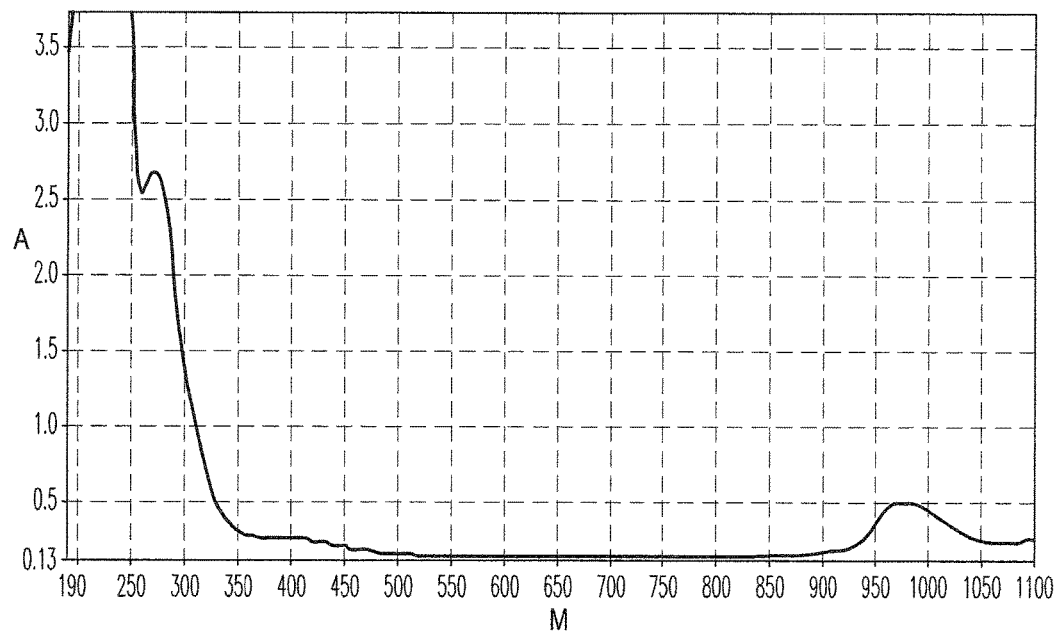
FIG. 1 shows the UV-vis absorption spectrum of silver nanoparticles synthesized by the inventive method.

A method of preparing metal nanoparticles from fungi can include preparing a biomass of fungal cells, providing an aqueous solution of a metal salt; mixing the biomass of fungal cells with the aqueous solution of a metal salt; and incubating the resulting mixture at a temperature range of about 35° C. to about 60° C. to produce the metal nanoparticles. The incubating step is preferably performed in the dark for about 24 hours. Preferably, the incubating step occurs at 45° C. The metal salt can be silver nitrate ($AgNO_3$), however other noble metal salts may also be used. Typically, the fungal cells are from *Alternaria pluriseptat, Alternaria alternate*, and mixtures thereof. The metal nanoparticles can be purified by centrifugation at 10,000 rpm for about 10 minutes, two times, before they are collected. The metal nanoparticles produced by the present method display a mean diameter of about 200 nm and the actual diameter can range from about 1 nm to about 300 nm. The metal (silver) nanoparticles are spherical, spheroidal, elongated spherical, rod-shaped, and/or faceted. The synthesis of the silver nanoparticles can be monitored and quantified using visible spectroscopy.

A method of decontaminating sewage water can include contacting sewage water with an effective amount of the silver nanoparticles produced from fungal cells for a time sufficient to remove microorganisms or pollutants from the sewage water. The method of decontaminating sewage water can further comprise adding sodium sulfate together with the silver nanoparticles. Use of noble metal nanoparticles, especially silver nanoparticles (AgNPs), in treatment of waste water is desirable because of their high surface area (surface/volume) ratio for adsorption of contaminants.

As used herein, the term "nanoparticle" refers to a particle having at least one dimension sized between 1 and 100 nanometers. In some embodiments, the nanoparticles disclosed herein are from about 1 nm to about 300 nm in diameter. The term "effective amount," as used herein and in the claims, refers to an amount of the nanoparticles sufficient to treat and/or lessen a pollutant and/or microbial activity in sewage water. The present method of preparing silver nanoparticles is a simple, cost effective, and non-toxic method, which can be easily scaled up for large scale synthesis. The silver nanoparticles prepared from fungal biomass as described herein can be highly efficient in the removal of pollutants and microbial organisms from sewage water.

The following examples will further illustrate the process of preparing the metal nanoparticles from fungi and their use in treating sewage water.

EXAMPLE 1

Fungal Biomass Preparation

Fungal organisms, namely *Alternaria pluriseptata* and *Alternaria alternate*, were grown on isolation media (potato dextrose agar (PDA)). Petri dishes and tubes were washed with ethanol and all biomass was collected. The harvested biomass was centrifuged, followed by washing with distilled water to remove any components of the medium. The biomass was placed in a flask containing 30 ml distilled water and incubated for about 24 hours. The biomass was filtered and the cell filtrate was collected and used for biosynthesis of silver nanoparticles.

EXAMPLE 2

Biosynthesis of Silver Nanoparticles

Figure 2:
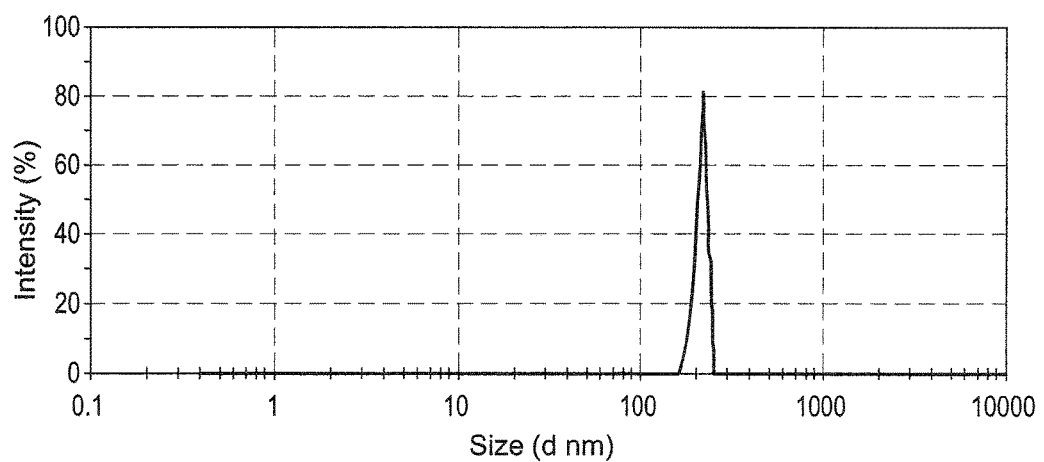
FIG. 2 is a plot of the particle size distribution of silver nanoparticles produced by the inventive method.
Figure 3B:
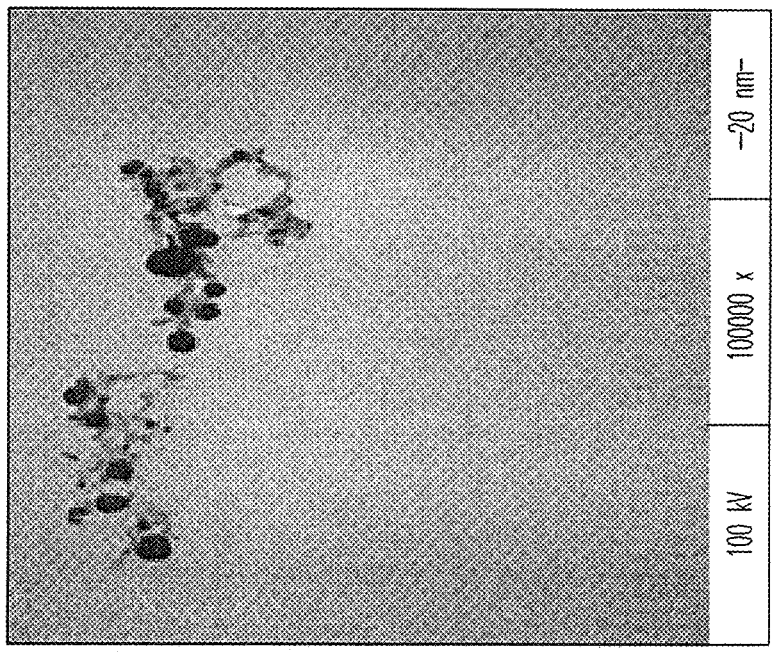
FIGS. 3A-3C show the transmission electron micrograph (TEM) of the silver nanoparticles produced by the inventive method.
Figure 3A:
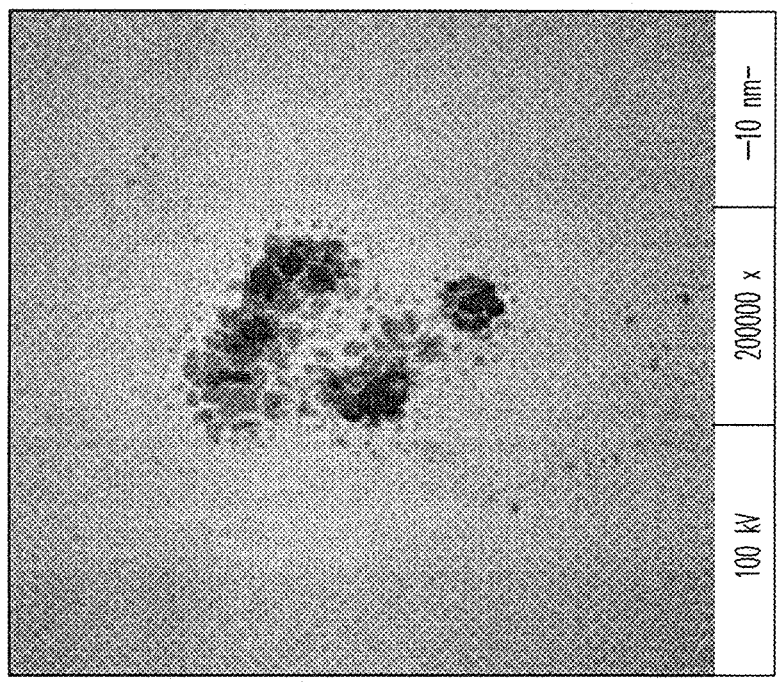
Figure 3C:
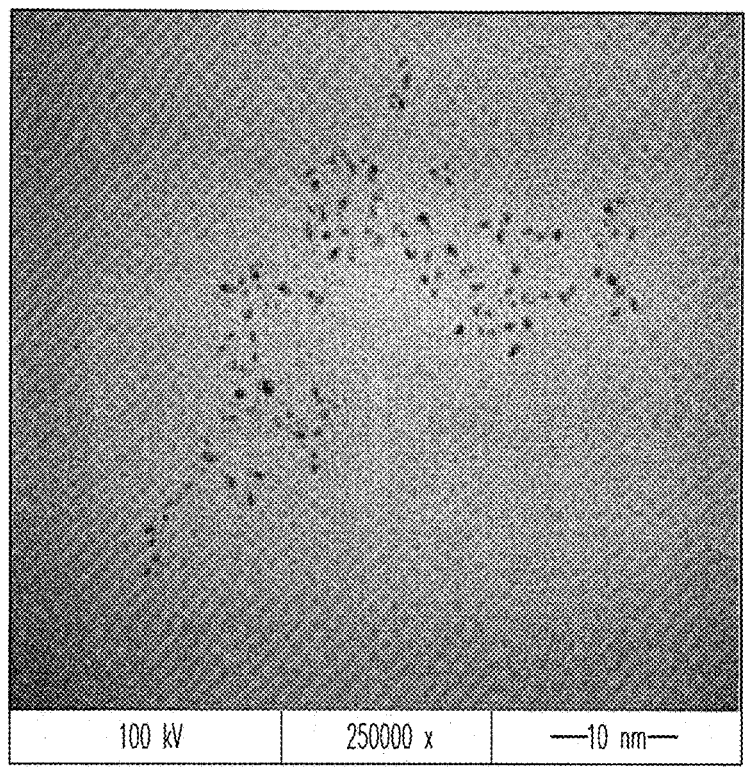

About 30 ml of biomass solution was mixed with (1 mM $AgNO_3$) silver nitrate aqueous solution in a flask. The mixture was incubated at 45° C. for 24 hours. The solution was kept in the dark to avoid any photochemical reactions during the experiment. The bio silver nanoparticles that were formed as a result of the reduction of the silver nitrate by the fungal biomass were isolated and purified by centrifugation at 10,000 rpm for 10 minutes two times. As the nanoparticles precipitated outside the cell, they were devoid of unnecessary cellular components. The isolated silver nanoparticles were characterized by UV-vis spectroscopy. FIG. 1 shows the UV-vis absorption spectrum of bio nano silver synthesized according to the present method. FIG. 2 shows the particle size distribution of the bio nano-silver particles having an average particle size distribution of 200 nm. FIG. 3A-3C shows the transmission electron micrograph (TEM) of the bio nano silver particles produced by the inventive method, which show silver nanoparticles having particle sizes ranging from 1 to 300 nm and having spherical shapes.

EXAMPLE 3

Treatment of Sewage Water Using Bio Silver Nanoparticles

About 5 ml of bio silver nanoparticles produced by the method of Example 2 was added to 1 liter of sewage water. Then it was set aside for about 3 to 5 days. Next, the treated water was filtered. The sewage water treated with the bio silver nanoparticles synthesized by fungal cells was tested and analyzed, and the resulting chemical characteristics of the treated sewage water are provided in Table 1.

TABLE 1

Chemical Characteristics of Sewage Water Treated With Bio Silver Nanoparticles

| TESTS | Name of Sample 1: S. FUNG[a] | Name of Sample 2: S. FUNG "SO PH"[b] | UNITS |
|---|---|---|---|
| Color | 348 | 316 | 5-50 units |
| Odor | — | — | Unobjectionable |
| Taste | — | — | Unobjectionalbe |
| Turbididty | 66 | 60 | 5-25 Unit |
| pH | 7.54 | 7.33 | 6.5-8.5 |
| Conductivity | 3454 | 3604 | 800-2300 ms/cm |
| TDS | 2576 | 2697 | 500-1500 mg/l |
| Free Chlorine | Nil | NIL | 0.2-0.5 mg/l |
| Total Hardness | 950 | 800 | 100-500 |
| Potassium | >3.5 | >3.5 | mg/l |
| Total iron | 0.6 | 0.5 | 0.1-1.0 mg/l |
| chloride | 900 | 80 | 200-600 mg/l |
| Nitrate | 19.1 | >100 | 0-45 mg/l |
| Nitrite | 0.04 | 0.046 | 0.00-0.00 mg/l |

TABLE 1-continued

Chemical Characteristics of Sewage Water Treated With Bio Silver Nanoparticles

| TESTS | Name of Sample 1: S. FUNG[a] | Name of Sample 2: S. FUNG "SO PH"[b] | UNITS |
|---|---|---|---|
| Sulfate | >130 | >130 | 200-400 mg/l |
| Fluoride | >1 | >1 | 0.6-1.0 mg/l |
| Silica as $SiO_2$ | 50 | >100 | mg/l |

[a]"S. Fung" represents sewage water treated by silver nanoparticles synthesized using fungi.
[b]"S. Fung SO PH" is sewage water treated with sodium sulfate and silver nanoparticles synthesized using fungi.

EXAMPLE 4

Treatment of Sewage Water Using Bio Silver Nanoparticles and Sodium Sulfate

About 5 ml of bio silver nanoparticles was added to 1 L of sewage water, then it was kept aside for about 3 to 5 days. Next, the treated water was filtered. Then, about 5 mg of sodium sulfate was added to the filtered and treated sewage water. The treated sewage water was tested. The results of chemical characteristics for the treated sewage water are provided in Table 1. The chemical characteristic for the treated sewage water was characterized using spectrophotometer, pH meter, T.D.S. meter (Total Dissolved Solids), and conductivity meter and titration tests.

It is to be understood that the present invention is not limited to the embodiments described above, but encompasses any and all embodiments within the scope of the following claims.

We claim:

1. A method of preparing silver nanoparticles from fungi comprising:
preparing a biomass of fungal cells, wherein the fungal cells are obtained from *Alternaria pluriseptat;*
providing an aqueous solution including a metal salt, wherein the metal salt is silver nitrate ($AgNO_3$);
mixing the biomass of fungal cells with the aqueous solution of metal salt to form a mixture; and
incubating the mixture at a temperature ranging from about 35° C. to about 60° C. to produce the silver nanoparticles, wherein the silver nanoparticles have a mean diameter of 200 nm.

2. The method of preparing metal nanoparticles from fungi according to claim 1, wherein the incubating is performed in the dark for at least 24 hours.

3. The method of preparing metal nanoparticles from fungi according to claim 1, wherein the incubating occurs at 45° C.

4. The method of preparing metal nanoparticles from fungi according to claim 1, further comprising isolating the metal nanoparticles from the fungal cells using centrifugation at 10,000 rpm for about 10 minutes.

5. The method of preparing metal nanoparticles from fungi according to claim 1, wherein the metal nanoparticles are spherical, spheroidal, elongated spherical, rod-shaped, and/or faceted.

6. A method of decontaminating water comprising:
contacting water with an effective amount of the metal nanoparticles produced according to the method of claim 1 for a time sufficient to remove microorganisms or pollutants from the water.

7. The method of decontaminating water according to claim 6, further comprising adding sodium sulfate to the water.

8. The method of decontaminating water according to claim 6, wherein the water is sewage water.

\* \* \* \* \*